(12) United States Patent
Merbouh et al.

(10) Patent No.: US 6,498,269 B1
(45) Date of Patent: Dec. 24, 2002

(54) METHOD FOR THE OXIDATION OF ALDEHYDES, HEMIACETALS AND PRIMARY ALCOHOLS

(75) Inventors: Nabyl Merbouh, Storrs; James M. Bobbitt, Mansfield Center; Christian Brückner, Norwich, all of CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/690,614

(22) Filed: Oct. 17, 2000

(51) Int. Cl.⁷ .......................... C07C 51/27; C07H 7/033
(52) U.S. Cl. ................ 562/515; 562/512; 562/523; 562/527; 562/540; 536/18.2
(58) Field of Search ................ 562/515, 523, 562/527, 512, 540; 536/18.2

(56) References Cited

U.S. PATENT DOCUMENTS 5,179,218 A    1/1993   Fried ................ 554/134

FOREIGN PATENT DOCUMENTS

| BE | BE 1 007 467 A | 7/1995 |
| WO | WO 95/07303 | 3/1995 |

OTHER PUBLICATIONS de Nooy, Arjan E. J., et al, "On the Use of Stable Organic Nitroxyl Radicals for the Oxidation of Primary and Secondary Alcohols", J. Synthetic Org. Chem., vol. 10, pp. 1153–1174 (1996).

de Nooy, Arjan E. J., et al, "Selective Oxidation of Primary Alcohols Mediated by Nitroxyl Radical in Aqueous Solution, Kinetics and Mechanism", Tetrahedron, vol. 51, pp. 8023–8032 (1995).

Bobbitt, James M., et al, "Organic Nitrosonium Salts as Oxidants in Organic Chemistry", Heterocycles, vol. 27, No. 2, pp. 509–533 (1988).

Mehltretter, et al, "Chemical Synthesis of D–Glucuronic Acid", Adv. Carbohydr. Chem. vol. 8, pp. 231–249 (1953).

Miyazawa, Takeo, et al, "Selective Oxidation of Alcohols by Oxoaminium Salts(R2N=O+X–)", J. Org. Chem., vol. 50, pp. 1332–1334, (1985).

Yamaguchi, Masao, et al, "Oxidation of Cycloalkanols to the Corresponding Cycloalkanones with Chlorine in the Presence of Nitroxide Radical as a Mediator", Bull. Chem. Soc. Jpn., vol. 63, pp. 947–949 (1990).

D.F. Shriver, et al. "Inorganic chemistry"(1990) Oxford Universy Press. p. 418.

*Primary Examiner*—Bernard Dentz
(74) *Attorney, Agent, or Firm*—Cantor Colburn LLP

(57) ABSTRACT

A method for the oxidation of substrates comprising treating an aqueous, basic solution of a substrate having an oxidizable functionality using an elemental halogen as terminal oxidant in the presence of an oxoammonium catalyst/halide co-catalyst system. Use of elemental halogen, preferably chlorine gas or elemental bromine, unexpectedly allows oxidation without significant degradation of the substrate. The substrate is preferably a monosaccharide, oligosaccharide, or polysaccharide, and the oxidizable functionality is preferably an aldehyde, hemiacetal, or a primary alcohol. An effective source of the oxoammonium catalyst is 2,2,6,6-tetramethylpiperidinyl-1-oxy (TEMPO) and a particularly economical and effective catalyst is 4-acetylamino-2,2,6,6-tetramethylpiperidinyl-1-oxy.

60 Claims, No Drawings

METHOD FOR THE OXIDATION OF ALDEHYDES, HEMIACETALS AND PRIMARY ALCOHOLS

TECHNICAL FIELD

The present invention relates generally to methods for the oxidation of aldehydes, hemiacetals, and primary alcohols. The method finds particular utility in the production of monosaccharide aldaric acids and polyuronic acids.

BRIEF DESCRIPTION OF THE RELATED ART

Carbohydrates, or saccharides, have great promise as a renewable resource in the large-scale production of chemicals for industrial, pharmaceutical, and home use. Not only is the promise of tapping a renewable resource of great economic interest, but a number of carbohydrate-based polymers have been shown to be biodegradable. These materials may therefore also satisfy growing environmental concerns. This appealing combination of advantages is, however, often offset by the unavailability of economical processes for the production of carbohydrate-based raw materials.

D-glucose (also known as dextrose) is the building block of starch, cellulose, and maltose, and is widely used in the food industry, as a feedstock for sorbitol production, and as a carbon source in industrial fermentations. It is currently produced on large industrial scale by the enzymatic hydrolysis of starch. However, broader industrial use of the oxidized forms of D-glucose is hampered by a number of problems, including reaction selectivity. Use of oxidized forms of oligocarbohydrates and polycarbohydrates (as phosphate-free detergent builders, metal chelators, and additives for glues, inks, and the like) is similarly limited by lack of reaction selectivity.

Glucaric acid, a diacid in which both terminal ends of the glucose molecule are in the forms of acid finctionalities, is an especially useful oxidation product of glucose. Not only glucaric acid, but carbohydrate-based acids (e.g. aldaric acids, polyuronic acids) in general show great promise as raw materials for the formation of biodegradable detergents, metal complexation agents (special sequestrants/ preservatives in, for instance, cooling fluids and or foods), biodegradable polymers for high tensile strength fibers, films, adhesives and plant fertilizers. Glucaric acid has also been shown to have anti-tumor and chemopreventive properties, cholesterol-lowering effects, and has been shown to be a viable chelating agent for radioisotopes of biomedical interest such as $^{99m}$Tc. This isotope is used for the radioimaging of tumors, bone structures and the early detection of myocardial infarction.

D-glucaric acid is generally made by direct oxidation of D-glucose as shown below:

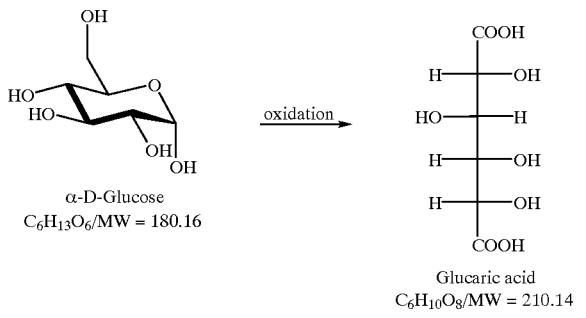

The current difficulty in obtaining D-glucaric acid on a commercial scale is reflected in its price, which is more than 100-fold that of glucose. Classic prior art methods for the production of glucaric acid from glucose use strong oxidants such as nitric acid or nitrogen oxides. These methods are characterized by low overall yields due to poor selectivity of these oxidations and large quantities of undesired degradation products formed. The number of side products and decomposition products formed require economically inefficient separation steps for the isolation of the glucaric acid or its salts. Other oxidation methods require use of expensive precious metal catalysts such as platinum, palladium, ruthenium or their oxides, or have other requirements, which render them less suitable for large-scale industrial processes, such as expensive and/or environmentally unfavorable solvents or reaction conditions.

Hypochloride ($M^+OCl^-$, bleach) and hypbromide ($M^+OBr^-$) are known to oxidize carbohydrates, but the reaction is characterized by long reaction times, destruction of the backbone of polymeric saccharides and thus low yields, on the order of 12% based on the starting material (Mehltretter, et al., Adv. Carbohydr. Chem. Vol. 8, pp. 231–249 (1953).

As reviewed by de Nooy et al. in Synthesis, Vol. 10, pp. 1153–1174 (1996), addition of a nitroxide-based catalyst to a sodium hypochloride solution results in improved yields, such that up to quantitative yields of oxidation product can be observed. The outcome of these oxidation reactions is strongly dependent on the particular reaction conditions chosen, as detailed by de Nooy, et aL in Tetrahedron, Vol. 51, pp. 8023–32 (1995). Oxidations using bleach are only possible with solutions containing no more than 15 weight percent of total dissolved solids, and addition of commercial bleach solution results in further dilution of the reaction mixture. Scale-up of this process is accordingly difficult, requiring larger and more expensive equipment, more space, and more energy, and generating more waste. Product isolation from dilute solutions is also more difficult.

Yamaguchi et al., in Bull. Chem. Soc. Jpn., Vol. 63, 947–948 (1990) disclose the oxidation of primary and secondary alcohols to using a nitroxide/chlorine system in organic solvents in yields in the range from bout 60 to 70%. The reported oxidation is non-selective, and thus unsuitable for use in oxidations of carbohydrate substrates such as glucose to the corresponding acids.

There accordingly remains a need in the art for efficient, environmentally favorable methods for the high yield production of carbohydrate diacids suitable for large-scale industrial production. It would be a further benefit if the method were generally applicable for the oxidation of aldehydes, hemiacetals, and primary alcohols in the presence of other functional groups.

SUMMARY OF THE INVETION

The above described drawbacks and disadvantages are alleviated by a method for the oxidation of substrates comprising treating an aqueous, basic solution of a substrate having an oxidizable functionality using an elemental halogen as terminal oxidant in the presence of an oxoammonium catalyst/halide co-catalyst system. In contrast to the prior art, use of elemental halogen, preferably chlorine gas or elemental bromine, unexpectedly allows selective oxidation without significant degradation of the substrate. The substrate is preferably a monosaccharide, oligosaccharide, or polysaccharide, and the oxidizable functionality is preferably an aldehyde, hemiacetal, or a primary alcohol. An effective source of the oxoammonium catalyst is based on 2,2,6,6-tetrarnethylpiperidinyl-1-oxy (TEMPO) and a particularly economical and effective catalyst is 4-acetylamnino-2,2,6,6-tetramethylpiperidinyl-1-oxy.

In a particularly preferred embodiment, a 5- or 6-carbon monosaccharide is oxidized to the corresponding aldaric acid, without substantial degradation of the backbone. The oxidized product may be isolated by filtration of the corresponding salts, or by acidification and extraction. The oxidation is highly selective for terminal groups, such that direct isolation of the product alkaline or alkaline metal salt from the reaction mixture yields analytically pure product.

This straightforward process produces highly desirable products in high yield and with high selectivity. Use of an inexpensive oxidant such as chlorine in an aqueous solvent allows for scaling up of the oxidation method to industrially relevant scales, thus providing significant advantages over other prior art methods. The above discussed and other features and advantages of the present invention will be appreciated and understood by those skilled in the art from the following detailed description.

DETAILED DESCRIPTION OF THE PREFERRED EMBODIMENTS

A high-yield, selective method for the oxidation of functional groups such as aldehydes, hemiacetals, and primary alcohols comprises treating an aqueous, basic solution of a substrate having an oxidizable functional group with an elemental halogen in the presence of a catalytic quantity of an oxoammonium catalyst/halide co-catalyst system. In an important and unexpected feature, use of elemental halogen does not result in the degradation of the substrate. In the case of the oxidation of D-glucose to D-glucaric acid, the reaction may result in the production of high yields (>90%) of analytically pure potassium salts, or the glucaric acid may be isolated by acidification and extraction.

Substrates suitable for oxidation have at least one oxidizable functional group, for example an aldehyde, hemiacetal, or primary alcohol. Under suitable conditions, other functional groups may also be oxidized, for example secondary alcohols, diols, polyols, phenols, thiols, thioethers, amines, imines, and alkylhalides Saccharides are a preferred substrate. Suitable saccharides have at least one functional group capable of oxidation, usually a terminal alcohol, a hemiacetal, or an aldehyde group. As used herein, "saccharide" refers to polyhydroxy aldehydes, hemiacetals, or ketones and their derivatives. "Derivatives" is intended to encompass both synthetic and naturally occurring variations in the basic polyhydroxy carbonyl structure, including but not being limited to substitutions and deletions, e.g., deoxy, deoxyamino, and sulfonate derivatives. Monosaccharides consist of a single polyhydroxy aldehyde, hemiacetal, or ketone unit, or a derivative of a single polyhydroxy aldehyde, hemiacetal, or ketone unit. Suitable monosaccharides include 3-, 4-, 5-, 6-, 7-, and 8-carbon and higher monosaccharides and their derivatives such as their X-deoxy-derivatives and aminosugars.

Suitable saccharides include trioses such as glyceraldehyde, tetroses such as erythrose, and threoses. Five- and six-carbon monosaccharides and their derivatives are most preferred, including but not limited to the D and L forms of sugars and their keto-analogs (ketoses) such as ribose, arabinose, xylose, lyxose, ribulose, and xylulose; as well as allose, altrose, glucose, mannose, gulose, idose, galactose, talose, psicose, fructose, sorbose, and tagatose. This method provides a convenient method for the conversion galactose to mucic acid and mannose to mannaric acid.

Other suitable substrates include oligosaccharides (having from two to about ten monosaccharide units) and polysaccharides (having more than about ten monosaccharide units), as well as derivatives of oligosaccharides and polysaccharides. Suitable oligosaccharides include, without limitation, maltose, lactose, cellobiose, gentibiose, and sucrose; as well as raffinose, melezitose, and cyclodextrins. Suitable polysaccharides include homopolysaccharides and their derivatives, for example cellulose, hemicelluloses, chitin, pectins, starches such as amylose and amylopectin, inulin, nigeran, pullulan, dextrans, fructans, mannans, xylans, and arabinans; and heteropolysaccharides, as are exemplified by agar(ose), alginic acid, gum Arabic, and glucosaminoglucans such as dermatan sulfate, chondroitin and hyaluronic acid. The foregoing lists are illustrative, rather than limiting.

While a significant advantage of the present method is its selectivity in the presence of secondary alcohol groups, the method is also suitable for use with saccharides (or other compounds) having derivatized (i.e., protected) alcohol groups. Other functional groups may also be present on the substrate, as long as the presence of such groups does not interfere with the oxidation. For convenience, the following discussion will be directed to a "saccharide", but it is to be understood that other compounds containing at least one oxidizable group are included.

In accordance with the present method, oxidizable saccharide is first dissolved in an aqueous, basic solution. Solvents other than water may be present as long as they do not interfere with the oxidation. Preferably, the dissolved solids (saccharide, base, catalyst, and co-catalyst) comprises up to about 20%, and more preferably, up to about 15% by weight of the aqueous solution. The pH of the solution is adjusted to at least about 9 to about 14, preferably at least about 10 to about 12, and most preferably from about 11 to about 11.5. Suitable agents for adjusting the pH include potassium hydroxide, sodium hydroxide, sodium carbonate, potassium carbonate, calcium hydroxide, and the like.

The solution further comprises an alkali or alkaline earth metal halide salt, for example potassium bromide, sodium bromide or sodium iodide. The halide acts as a co-catalyst in the oxidation reaction, and is thus preferably present in an amount of about 0.01 to about 0.3, preferably about 0.10 to about 0.25, and most preferably about 0.15 equivalents, based on the amount of oxidizable saccharide groups.

The solution still further comprises an oxammonium catalyst, preferably in catalytic quantities. As used herein (and explained in greater detail below), "oxoammonium catalyst" denotes the catalytic species generated from the addition of a stabilized nitroxide, oxoammonium salt, and/or hydroxylamine to an aqueous, basic solution comprising a halide and an elemental halogen. Nitroxides have the structure (1); the salt forms of their oxidation products, oxammonium salts, have the structure (2); and the corresponding hydroxylarnines have the structure (3):

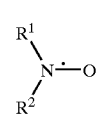

(1)

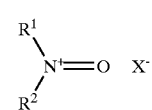

(2)

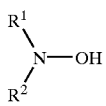

(3)

wherein each of R[1] and R[2] are the same or different, being alkyl, aryl, cycloalkyl aryl, a heteroatom substituted alkyl or aryl, or taken together, a cycloalkyl group, the groups having from 1 to about 35 carbons; and X is an anionic species, preferably inorganic, for example, chloride, bromide, perchlorate or perbromate. Preferably, no hydrogen atoms are bound to the carbons directly adjacent the oxoarnmonium nitrogen.

Particularly preferred catalysts are based on 2,2,6,6-tetrasubstituted piperidines having the structure (4), (5), or (6):

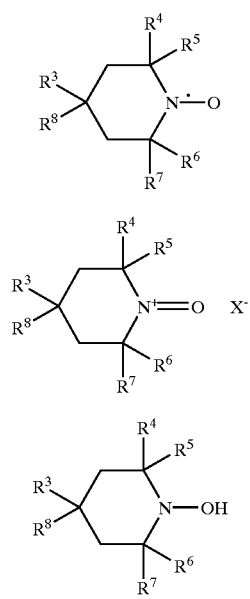

wherein each of R[4], R[5], R[6], and R[7] is the same or different, being an alkyl, aryl, or heteroatom-substituted alkyl group, each group having from 1 to about 15 carbons; each of R[3] and R[8] is the same or different, being a hydrogen, alkyl, aryl, heteroatom substituent, or, taken together, oxygen; and X is an anionic group, preferably inorganic. Preferably, R[4], R[5], R[6], and R[7] are methyl, ethyl, propyl, or butyl groups.

In addition to hydrogen, the heteroatom substituent may include halogen, oxygen, nitrogen, and the like. Preferably, one of R[3] and R[8] is hydrogen while the other is a heteroatom substituent that does not interfere with the reaction. Suitable heteroatom substituents include but are not limited to —OR[1], —OC(O)R[1], —NHC(O)R[1], —N(CH$_3$)$_3$Cl, —OSO$_3$H, and the like. Taken together, R[3] and R[4] may form a carbonyl group.

Without being bound by theory, it is presently hypothesized that upon dissolution of an elemental halide in an aqueous, basic solution, the corresponding hypohalide is formed. The hypohalide then oxidizes the nitroxide species to the corresponding oxammonium species, which is presumed to be the active form of the catalyst. Upon oxidizing the substrate, the oxammonium species is reduced to the corresponding hydroxylamine. The hydroxylamine syn conproportionates with an equivalent of oxammonium to form two equivalents of nitroxide, closing the catalytic cycle. These catalytic cycles make it possible to use the nitroxide, hydroxylamine, or oxoammonium catalyst and halide co-catalyst in catalytic quantities. In a preferred embodiment, elemental chlorine and a metal bromide salt is used. In this case, it is hypothesized that the hypochloride oxidizes the bromide anion to hypobromide, which oxidizes nitroxides to oxoammonium faster than hypochlorides.

It is because the oxoammonium species is presently hypothesized to oxidize the substrate that the phrase "oxoammonium catalyst" is used herein. However, it is to be understood that the catalyst may in fact be a different species, and that the term "oxoammonium catalysts" means that catalyst or catalyst system formed by the addition of an effective stabilized nitroxide, oxoammonium salt, and/or hydroxylamine to an aqueous, basic solution comprising a halide and an elemental halogen. Such species are generally known in the art. For example, oxidation of a nitroxide precursor to form an isolated, oxoammonium salt (3) is described in J. Organic Chemistry, Vol. 50, 1332 (1985). Bobbitt and Flores provide a list of methods for the preparation of oxoammonium salts in Heterocycles, Vol. 27, No. 2, 509–533 (1988).

2,2,6,6-Tetramethylpiperidinyl-1-oxy derivatives are presently preferred for reasons of both safety and cost, for example, 4-acetylamino-2,2,6,6-tetramethylpiperidinyl-1-oxy, 4-hydroxy-2,2,6,6-tetramethylpiperidinyl-1-oxy, 4-oxo-2,2,6,6-tetramethylpiperidinyl-1-oxy, and 4-methoxy-2,2,6,6-tetramethylpiperidinyl-1-oxy. A preferred oxoammonium salt is 4-acetylamino-2,2,6,6-tetramethylpiperidine-1-oxoammmonium tetrafluoroborate.

An effective amount of catalyst may vary widely, and is readily determined by one of ordinary skill in the art, depending on cost, effectiveness, and the like. In general, from about 0.001 to 0.1 equivalents of catalyst (based on the oxidizable groups) is effective.

The above-described pH-adjusted aqueous solution of saccharide, salts, and catalyst is preferably chilled prior to introduction of the oxidant and maintained at a lower temperature over the course of the reaction in order to maintain the selectivity of the reaction and to minimize side products. Temperatures in the range from about 0 to about 60° C., about 0 to about 20° C., about 0 to about 10° C., and most preferably from about 0 to about 5° C. are preferred.

After chilling, the elemental halogen (chlorine, bromine, or iodine) is next introduced into the aqueous solution. Preferred halogens are gaseous chlorine ($Cl_2$) or liquid bromine ($Br_2$). Gaseous chlorine is one of the least expensive oxidants available, and is well suited to industrial scale processes. The incoming stream of $Cl_2$ can be diluted, to up to about 1% by volume of $Cl_2$ with nitrogen, air, or other inert gas for better dissipation of the heat of reaction and/or the heat generated by dissolution of $Cl_2$ in the aqueous solution. The amount of $Cl_2$ required is at least one half equivalent per desired oxidation equivalent as defined as electrons involved in the oxidation process. The halogen is preferably introduced into the solution at a rate effective to prevent the temperature of the solution to rise above the ceiling temperature determined ideal for the reaction (e.g., 5° C.). Liquid bromine provides ease of handling for laboratory purposes. The amount of $Br_2$ used is at least one half equivalent per desired oxidation equivalent.

During oxidation, the pH of the solution is preferably maintained in the range from about 10 to about 11.5, preferably in the range from about 11 to about 11.5, and most preferably at about 11.5. The pH may be conveniently adjusted by the addition of a concentrated aqueous solution of a base, such as a 2 molar solution of sodium hydroxide or potassium hydroxide.

After completion of the oxidation, the product acid may be isolated by conventional means. In a particularly advantageous feature, using potassium hydroxide or carbonate as a base, the potassium salt of D-glucaric acid may be obtained by adding 1 equivalent of concentrated acid (e.g., HCl) to the solution, followed by filtration of the crystalline salt, which is analytically pure. Adjusting the pH of the mother liquor to 3.4 and reducing the volume by about one-third yields a second crop, bringing the total yield of the reaction to about 80 to about 90%, based on starting glucose. Use of filtration to isolate the product diacid derivative or salt is particularly valuable feature, especially as purification of saccharides can be difficult.

Using sodium hydroxide or carbonate as a base, the sodium salt of D-glucaric acid can be isolated by reducing the volume of the reaction solution by about one-third, and adding about four volumes of ethanol to yield the sodium salt in the form of a syrup. The mother liquor is decanted, the syrup is dissolved in water, precipitated with ethanol, and the mother liquor is again decanted. The procedure is repeated until the desired level of purity is obtained.

Alternatively, the sodium salt may be converted to the potassium salt and then isolated as described above. For example, the crude glucaric acid disodium salt may be passed as an aqueous solution through an ion exchange resin in its hydrogen ion form. The pH of the resulting aqueous solution of glucaric acid is then adjusted to 3.4 with aqueous potassium hydroxide and the potassium salt is then isolated as described above. Or, one equivalent of a concentrated acid such as HCl and 3–4 equivalents of KCl may be added to the aqueous solution of the crude glucaric acid disodium salt, whereupon which the glucaric acid monopotassium salt precipitates and is isolated by filtration.

In yet another variation, 1 equivalent of $CaCl_2$ can be added to the warm (about 45° C.) solution of the disodium or dipotassium salt of glucaric acid, whereupon the calcium salt of glucaric acid as its monohydrate crystallizes and can be isolated by filtration.

Where sodium or potassium hydroxide and sodium or potassium halides are used, the side products of the above-described method are primarily water and sodium chloride (rock salt, NaCl) or potassium chloride (KCl) Sodium chloride and potassium chloride are starting materials for the industrial synthesis of chlorine and potassium or sodium hydroxide (KOH or NaOH). The above-described process is accordingly a closed-loop process, which generates minimal waste products.

The present process provides an efficient, environmentally favorable method for the production of saccharide diacids, which have heretofore been unavailable on large, industrial scale. Use of elemental halogens allows for the use of one of the cost-effective oxidants available in industry and reaction of more concentrated solutions with minimal degradation of the saccharide backbone. Use of the nitroxide-based catalysts allows their use as heterogeneous catalysts in biphasic systems using phase transfer catalysis or heterogenized (solid phase bound) catalysts, thus allowing an easier recovery of the catalyst.

The invention is further illustrated by the following non-limiting examples. All references cited herein are incorporated by reference in their entirety.

EXAMPLES

Example 1

Conversion of Glucose to Monopotassium Glucarate

To an aqueous solution (50 mL) of glucose (3 g) is added KBr (400 mg), a nitroxide catalyst (4-acetylamino-2,2,6,6-tetramethylpiperidine-1-oxy, 40 mg) and an aqueous KOH solution (6.51 g in 30 mL water). The solution is chilled to 0C and gaseous chlorine is bubbled through a glass frit into the solution at a rate so not to allow the temperature of the stirred solution to rise over 5° C. The pH of the solution is held constant at 11.5 through addition of a 2 molar solution of KOH by an autotitrator. Reaction progress is followed by $^{13}C$ NMR. Once the signal indicative of the primary alcohol group in glucose had disappeared (about 63 ppm, $D_2O$, 25° C.), the addition of chlorine is stopped and the solution is flushed with nitrogen. Concentrated HCl is added to the chilled solution until pH 3.4 is reached. The precipitated monopotassium glucarate is isolated by filtration through a glass-fritted funnel. The mother liquor is concentrated in vacuo to one-third of its original volume, never allowing the temperature to rise above 40° C. The second crop of product is filtered. The yield of the combined dried product is 75–90% (3.1–3.7 g). Recrystallization from a 2.5-fold quantity (by weight) of boiling water yields analytically pure (chloride-free) material as tested by optical rotation, melting point, $^{1}H$ and $^{13}C$ NMR, elemental analysis, and comparison to genuine material.

Example 2

Conversion of Glucose to Disodium Glucarate

To an aqueous solution (50 mL) of glucose (3 g) is added NaBr (400 mg), nitroxide catalyst (4-acetylamino-2,2,6,6-tetrarnethylpiperidine-1-oxy, 40 mg) and an aqueous NaOH solution (4.4 g in 30 mL water). The solution is chilled to 0° C. and gaseous chlorine is bubbled through a glass frit into the solution at a rate so not to allow the temperature of the stirred solution to rise over 5° C. The pH of the solution is held constant at 11.5 through addition of a 2 molar solution of NaOH by means of an autotitrator. Reaction progress is followed by $^{13}C$ NMR. Once the signal indicative of the primary alcohol group in glucose had disappeared (about 63 ppm, $D_2O$, 25° C.), the addition of chlorine is stopped and the solution is flushed with nitrogen. The pH is adjusted to 8.0 by adding 1 molar aqueous HCl. The solution is then concentrated to about 30 mL, and the disodium glucarate is precipitated by addition of ethanol (100 mL, 95%). The mother liquor is decanted from the precipitated gum. The gum is dissolved in 30 nL of water and the precipitation operation is repeated as described above. The resulting residue was finally washed with a mixture of ethanol-water (4:1) and dried at 40° C. under reduced pressure. The yield of the dried product is 75–90% (3.2–3.8 g). A chloride analysis performed on this samples indicates a chloride contents of less than 1% by weight.

Example 3

Conversion of Galactose to Mucic Acid

To an aqueous solution (50 mL) of galactose (3 g) is added KBr (400 mg), nitroxide catalyst (4-acetylamino-2,2, 6,6-tetramethylpiperidine-1-oxy, 40 mg) and an aqueous KOH solution (6.51 g in 30 mL water). The solution is chilled to 0° C. and gaseous chlorine is bubbled through a glass frit into the solution at a rate so not to allow the temperature of the stirred solution to rise over 5° C. The pH of the solution is held constant at 11.5 through addition of a 2molar solution of KOH by means of an autotitrator. Reaction progress is followed by $^{13}C$ NMR. Once the signal indicative of the primary alcohol group in galactose had disappeared (~63 ppm, $D_2O$, 25° C.), the addition of chlorine is stopped and the solution is flushed with nitrogen.

Concentrated HCl is added to the chilled solution until pH 1.5–2.0 is reached. The precipitated mucic acid is isolated by filtration through a glass-fritted fimnel. The yield of the dried product is 75–80% (2.6–2.7 g). Analysis (up to 1% w/w chloride) material as tested by optical rotation, melting point, $^1H$ and $^{13}C$ NMR and elemental analysis and comparison to genuine material.

Example 4

Conversion of Maltose to O-α-D-Glucopyranosyluronic Acid-(1→4)-D-glucaric Acid

To an aqueous solution (50 mL) of maltose (3 g) is added NaBr (400 mg), nitroxide catalyst (4-acetylamino-2,2,6,6-tetramethylpiperidine-1-oxy, 40 mg) and aqueous NaOH (3.5 g in 30 mL water). The solution is chilled to 0° C. and gaseous chlorine is bubbled through a glass frit into the solution at a rate so not to allow the temperature of the stirred solution to rise over 5° C. The pH of the solution is held constant at 11.5 through addition of a 2 molar solution of NaOH by means of an autotitrator. Reaction progress is followed by $^{13}C$ NMR. Once the signal indicative of the primary alcohol groups in maltose had disappeared (about 60 ppm, $D_2O$, 25° C.), the addition of chlorine is stopped, and the solution is flushed with nitrogen. The pH is adjusted to 8.0 by adding 1 molar aqueous HCl. Then the solution is concentrated to about 30 mL, and the tricarboxylate is precipitated by addition of ethanol (100 mL). The precipitate is then dissolve in of water (30 mL) and the precipitation operation is repeated. The resulting gum was washed with a mixture of ethanol-water (4:1) and dried at 40° C. under reduced pressure to produce 2.9–3.2 g of material. The $^{13}C$ NMR shows more than 95% of conversion of the primary alcohols to carboxylic acids and a small quantity of oxalic acid. The structure was confirmed by comparison of the $^{13}C$ NMR data of the material produced with data published in the literature.

Example 5

Conversion of Starch to Sodium Polyglucuronate

To an aqueous solution (50 mL) of starch (3 g) is added NaBr (400 mg), nitroxide catalyst (4-acetylamino-2,2,6,6-tetramethylpiperidine-1-oxy, 40 mg) and aqueous NaOH (4.88 g in 30 mL water). The solution is chilled to 0° C. and gaseous chlorine is bubbled through a glass frit into the solution at a rate so not to allow the temperature of the stirred solution to rise over 5° C. The pH of the solution is held constant at 10.5 through addition of a 2M solution of NaOH by means of an autotitrator. Reaction progress is followed by $^{13}C$ NMR. Once the signal indicative of the primary alcohol group had disappeared, (about 60 ppm, $D_2O$, 25° C.), the addition of chlorine is stopped and the solution is flushed with nitrogen. The pH is adjusted to 8.0 by adding 1 molar aqueous HCl. Then the solution is concentrated to about 30 mL, and the oxidized saccharide is precipitated by adding of ethanol (100 mL). The precipitate is dissolve in water (30 mL) and the precipitation operation is repeated. The precipitated gum was washed with a mixture of ethanol-water (4:1) and dried at 40° C. under reduced pressure. The yield of the dried product is 2.5–3 g. The $^{13}C$ NMR of the product shows more than 95% of the primary alcohols were converted to carboxylic acids and the data is identical to independently prepared material.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An oxidative method, comprising:

treating an aqueous, basic solution of a substrate having an oxidizable functionality selected from the group consisting of aldehyde, hemiacetal, and primary alcohol with an elemental halogen in the presence of an oxoanmionium catalyst and halide co-catalyst.

2. The method of claim 1, wherein the pH of the basic solution is from about 9 to about 14.

3. The method of claim 1, wherein the pH of the basic solution is from about 10 to about 12.

4. The method of claim 1, wherein the pH of the basic solution is from about 11 to about 11.5.

5. The method of claim 1, wherein the elemental halogen is chlorine or bromine.

6. The method of claim 1, wherein the chlorine is introduced into the oxidation in the form of gas, diluted up to about 1% by volume with an inert gas.

7. The method of claim 1, wherein the source of the oxoammonium catalyst is at least one of a stabilized nitroxide (1), oxoammonium salt (2), hydroxylamine (3):

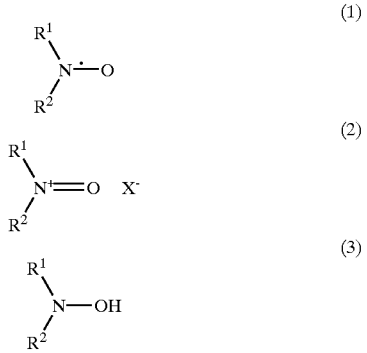

wherein each of $R^1$ and $^2$ are the same or different, being alkyl, cycloalkyl aryl, a heteroatom substituted alkyl or aryl, or taken together, a cycloalkyl group, the groups having from 1 to about 35 carbons; and X is an anionic species.

8. The method of claim 7, wherein the source of the oxoammonium catalyst has the structure (4), (5), or (6):

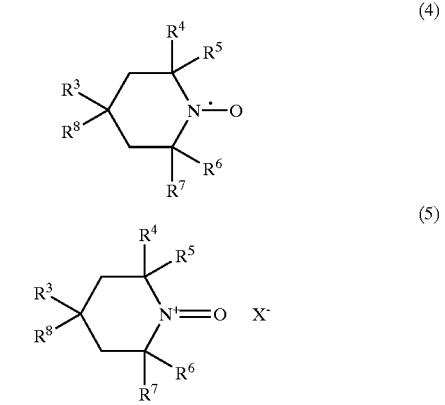

-continued (6)

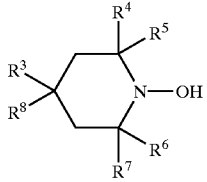

wherein each of $R^4$, $R^5$, $R^6$, and $R^7$ is the same or different, being an allyl, aryl, or heteroatom-substituted alkyl group, each group having from 1 to about 15 carbons; each of $R^3$ and $R^8$ is the same or different, being a hydrogen, alkyl, aryl, heteroatom substituent, or taken together, a carbonyl; and X is an anionic group.

9. The method of claim 8, wherein $R^4$, $R^5$, $R^6$, and $R^7$ are methyl, ethyl, propyl, or butyl groups; and one of $R^3$ and $R^8$ is hydrogen while the other is a heteroatom substituent selected from the group consisting of —$OR^1$, —$OC(O)R^1$, —$NHC(O)R^1$; and X is perchlorate or tetrafluoroborate.

10. The method of claim 9, wherein $R^4$, $R^5$, $R^6$, and $R^7$ are each methyl; one of one of $R^3$ and $R^8$ is hydrogen while the other is —$OR^1$, —$OC(O)R^1$, —$NHC(O)R^1$, —$N(CH_3)_3Cl$, and —$OSO_3H$.

11. The method of claim 10, wherein the oxoammonium catalyst is supplied to the oxidation in the form of 4-acetylamino-2,2,6,6-tetramethylpiperidine-1-oxy or 4-acetylamino-2,2,6,6-tetramethylpiperidine-1-oxoammmonium tetrafluoroborate.

12. The method of claim 1, wherein the oxidation is conducted at about 0° C. to about 20° C.

13. An oxidative method, comprising:
    treating an aqueous, basic solution of a saccharide having at least one oxidizable functionality with an elemental halogen in the presence of an oxoammonium catalyst and halide co-catalyst.

14. The method of claim 13, wherein the pH of the basic solution is from about 9 to about 14.

15. The method of claim 13, wherein the pH of the basic solution is from about 10 to about 12.

16. The method of claim 13, wherein the pH of the basic solution is from about 11 to about 11.5.

17. The method of claim 13, wherein the saccharide is the D or L forms of ribose, arabinose, xylose, lyxose, ribulose, xylulose, allose, altrose, glucose, mannose, gulose, idose, galactose, talose, psicose, fructose, sorbose, tagatose, maltose, lactose, cellobiose, gentibiose, sucrose, raffinose, melezitose, a cyclodextrin, cellulose, hemicellulose, amylose, amylopectin, dextran, fructan, mannan, xylan, arabinans, agar, pectins, alginic acid, gum Arabic, hyaluronic acid, chitin, murein, or glucosaminoglucan.

18. The method of claim 13, wherein the total dissolved solids comprises up to about 20% of the solution by weight.

19. The method of claim 13, wherein the substrate comprises up to about 15% of the solution by weight.

20. The method of claim 13, wherein the oxidizable group is an aldehyde, hemiacetal, or primary alcohol.

21. The method of claim 13, wherein the elemental halogen is chlorine or bromine.

22. The method of claim 21, wherein the chlorine is supplied to the oxidation mixed with from about 1 to about 99% by volume with an inert gas.

23. The method of claim 13, wherein the source of the oxoammonium catalyst is at least one of a stabilized nitroxide (1), oxoanunonium salt (2), or hydroxylamine (3):

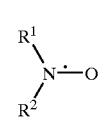

(1)

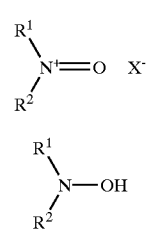

(2)

(3)

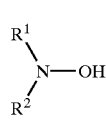

wherein each of $R^1$ and $R^2$ are the same or different, being alkyl, cycloalkyl aryl, a heteroatom substituted alkyl or aryl, or taken together, a cycloalkyl group, the groups having from 1 to about 35 carbons; and X is an anionic species.

24. The method of claim 23, wherein the source of thd oxoammonium catalyst has the structure (4), (5), or (6):

(4)

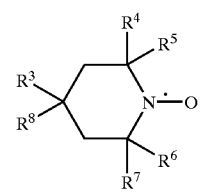

(5)

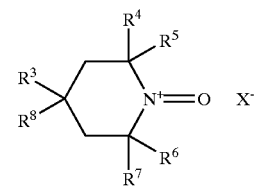

(6)

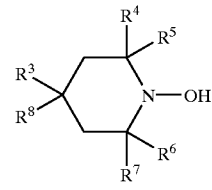

wherein each of $R^4$, $R^5$, $R^6$, and $R^7$ is the same or different, being an alkyl, aryl, or heteroatom-substituted alkyl group, each group having from 1 to about 15 carbons; each of $^3$ and $R^8$ is the same or different, being a hydrogen, alkyl, aryl, heteroatom substituent, or taken together, a carbonyl; and X is an anionic group.

25. The method of claim 24, wherein $R^4$, $R^5$, $R^6$, and $R^7$ are methyl, ethyl, propyl, or butyl groups; and one of $R^3$ and $R^8$ is hydrogen while the other is a heteroatom substituent selected from the group consisting of —$OR^1$, —$OC(O)R^1$, —$NHC(O)R^1$; and X is perchlorate or tetrafluoroborate.

26. The method of claim 25, wherein $R^4$, $R^5$, $R^6$, and $R^7$ are each methyl; one of one of $R^3$ and $R^8$ is hydrogen while the other is —$OR^1$, —$OC(O)R^1$, —$NHC(O)R^1$, —$N(CH_3)_3Cl$, and —$OSO_3H$.

27. The method of claim 25, wherein the oxoammonium catalyst is supplied to the oxidation in the form of 4-acetylamino-2,2,6,6-tetramethylpiperidine-1-oxy or 4-acetylamino-2,2,6,6-tetramethylpiperidine-1-oxoammmonium tetrafluoroborate.

28. The method of claim 25, wherein the saccharide is glucose, galactose, maltose, or starch.

29. The method of claim 25, wherein the oxidation is conducted at about 0° C. to about 5° C.

30. An oxidative method, comprising:

treating an aqueous, basic solution of a saccharide having at least one oxidizable functionality with an elemental halogen in the presence of an oxoammonium catalyst and a halide co-catalyst at about 5 to about 10° C., wherein the pH of the solution is maintained at about 9 to about 14.

31. The method of claim 30, wherein the pH of the oxidation is maintained at about 10 to about 12.

32. The method of claim 30, wherein the pH of the oxidation is maintained at about 11 to about 11.5.

33. The method of claim 30, wherein the oxidizable functionality is an aldehyde, hemiacetal, or primary alcohol.

34. The method of claim 30, wherein the saccharide is the D or L forms of ribose, arabinose, xylose, lyxose, ribulose, xylulose, allose, altrose, glucose, mannose, gulose, idose, galactose, talose, psicose, fructose, sorbose, tagatose, maltose, lactose, cellobiose, gentibiose, sucrose, raffinose, melezitose, a cyclodextrin, cellulose, hemicellulose, amylose, amylopectin, dextran, fiructan, mannan, xylan, arabinans, agar, pectins, algmnic acid, gum Arabic, hyaluronic acid, chitin, murein, or glucosaminoglucan.

35. The method of claim 34, wherein the saccharide is glucose, galactose, maltose, or starch.

36. The method of claim 30, wherein the elemental halogen is chlorine or bromine.

37. The method of claim 36, wherein the chlorine is introduced into the oxidation in the form of gas, diluted up to about 1% by volume with an inert gas.

38. The method of claim 30, wherein the source of the oxoammonium catalyst is at least one of a stabilized nitroxide (1), oxoammonium salt (2), or hydroxylamine (3):

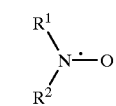

(1)

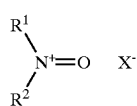

(2)

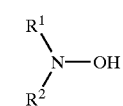

(3)

wherein each of $R^1$ and $R^2$ are the same or different, being alkyl, cycloalkyl aryl, a heteroatom substituted alkyl or aryl, or taken together, a cycloalkyl group, the groups having from 1 to about 35 carbons; and X is an anionic species.

39. The method of claim 30, wherein the source of the oxoammonium catalyst has the structure (4), (5), or (6):

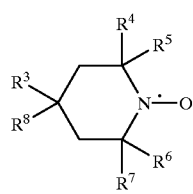

(4)

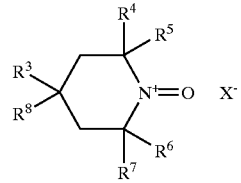

(5)

(6)

wherein each of $R^4$, $R^5$, $R^6$, and $R^7$ is the same or different, being an alkyl, aryl, or heteroatom-substituted alkyl group, each group having from 1 to about 15 carbons; each of $R^3$ and $R^8$ is the same or different, being a hydrogen, alyl, aryl, heteroatom substituent, or carbonyl; and X is an anionic group.

40. The method of claim 30, wherein $R^4$, $R^5$, $R^6$, and $R^7$ are methyl, ethyl, propyl, or butyl groups; and one of $R^3$ and $R^8$ is hydrogen while the other is a heteroatom substituent selected from the group consisting of —$OR^1$, —$OC(O)R^1$, —$NHC(O)R^1$; and X is perchlorate or tetrafluoroborate.

41. The method of claim 30, wherein $R^4$, $R^5$, $R^6$, and $R^7$ are each methyl; one of one of $R^3$ and $R^8$ is hydrogen while the other is —$OR^1$, —$OC(O)R^1$, —$NHC(O)R^1$, —$N(CH_3)_3Cl$, and —$OSO_3H$.

42. The method of claim 30, wherein the oxoammonium catalyst is supplied to the oxidation in the form of 4-acetylamino-2,2,6,6-tetramethylpiperidine-1-oxy or 4-acetylamino-2,2,6,6-tetrainethylpiperidine-1-oxoammmonium tetrafluoroborate.

43. An oxidative method, comprising:

treating an aqueous, basic solution of a saccharide having at least one aldehyde, hemiacetal, or primary alcohol with elemental chlorine, iodine, or bromine in the presence of a chloride, bromide, or iodide co-catalyst and a catalyst derived from at least one of a stabilized nitroxide (1), oxoaimmonium salt (2), or hydroxylamine (3):

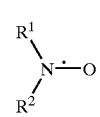

(1)

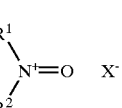

(2)

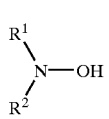

(3)

wherein each of $R^1$ and $R^2$ are the same or different, being alkyl, cycloalkyl aryl, a heteroatom substituted alkyl or aryl, or taken together, a cycloalkyl group, the groups having from 1 to about 15 carbons; and X is an anionic species.

44. The method of claim 43, wherein the source of the catalyst has the structure (4), (5), or (6):

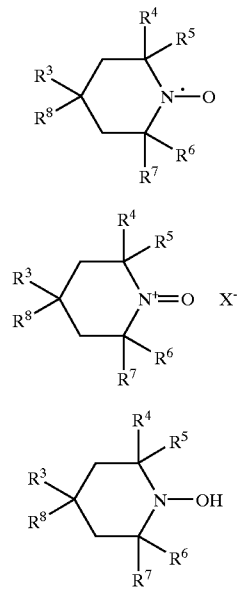

wherein each of $R^4$, $R^5$, $R^6$, and $R^7$ is the same or different, being an alkyl, aryl, or heteroatom-substituted alkyl group, each group having from 1 to about 15 carbons; each of $R^3$ and $R^8$ is the same or different, being a hydrogen, alkyl, aryl, heteroatom substituent, or taken together a carbonyl; and X is an anionic group.

45. The method of claim 44, wherein $R^4$, $R^5$, $R^6$, and $R^7$ are methyl, ethyl, propyl, or butyl groups; and one of $R^3$ and $R^8$ is hydrogen while the other is a heteroatom substituent selected from the group consisting of —$OR^1$, —$OC(O)R^1$, —$NHC(O)R^1$; and X is perchlorate or tetrafluoroborate.

46. The method of claim 45, wherein $R^4$, $R^5$, $R^6$, and $R^7$ are each methyl; one of one of $R^3$ and $R^8$ is hydrogen while the other is —$OR^1$, —$OC(O)R^1$, —$NHC(O)R^1$, —$N(CH_3)_3Cl$, and —$OSO_3H$.

47. The method of claim 43, wherein the catalyst is supplied to the oxidation in the form of 4-acetylamino-2,2,6,6-tetramethylpiperidine-1-oxy or 4-acetylamino-2,2,6,6-tetramethylpiperidine-1-oxoammmonium tetrafluoroborate.

48. The method of claim 43, wherein the saccharide is the D or L forms of ribose, arabinose, xylose, lyxose, ribulose, xylulose, allose, altrose, glucose, mannose, gulose, idose, galactose, talose, psicose, fructose, sorbose, tagatose, maltose, lactose, cellobiose, gentibiose, sucrose, raffinose, melezitose, a cyclodextrin, cellulose, hemicellulose, amylose, amylopectin, dextran, fructan, mannan, xylan, arabinans, agar, pectins, alginic acid, gum Arabic, hyaluronic acid, chitin, murein, or glucosaminoglucan.

49. The method of claim 43, wherein the saccharide is glucose, galactose, maltose, or starch.

50. The method of claim 45, wherein chlorine is introduced into the oxidation in the form of gas, diluted up to about 1% by volune with an inert gas.

51. The method of claim 43, wherein the pH of the oxidation is maintained at about 5 to about 0° C.

52. The method of claim 43, wherein the pH of the oxidation is maintained at about 11 to about 11.5.

53. An oxidative method, comprising:
treating an aqueous, basic solution of glucose, galactose, maltose, or starch with elemental chlorine or bromine at a pH in the range from about 9 to about 14 in the presence of a chloride, bromide, or iodide co-catalyst and a catalyst derived from at least one of a stabilized nitroxide (1), oxoanmonium salt (2), or hydroxylamine (3):

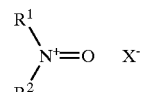

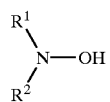

wherein each of $R^1$ and $R^2$ are the same or different, being alkyl, cycloalkyl aryl, a heteroatom substituted alkyl or aryl, or taken together, a cycloalkyl group, the groups having from 1 to about 35 carbons; and X is an anionic species.

54. The method of claim 53, wherein the source of the catalyst has the structure (4), (5), or (6):

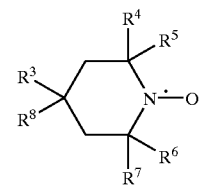

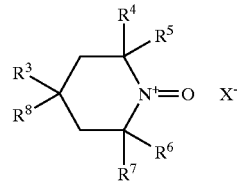

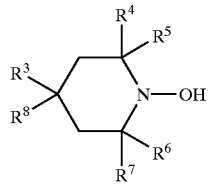

wherein each of $R^4$, $R^5$, $R^6$, and $R^7$ is the same or different, being an alkyl, aryl, or heteroatom-substituted alkyl group, each group having from 1 to about 15 carbons; each of $R^3$ and $R^8$ is the same or different, being a hydrogen, alkyl, aryl, heteroatom substituent, or taken together a carbonyl; and X is an anionic group.

55. The method of claim 54, wherein $R^4$, $R^5$, $R^6$, and $R^7$ are methyl, ethyl, propyl, or butyl groups; and one of $R^3$ and $R^8$ is hydrogen while the other is a heteroatom substituent selected from the group consisting of —$OR^1$, —$OC(O)R^1$, —$NHC(O)R^1$; and X is perchlorate or tetrafluoroborate.

56. The method of claim 55, wherein $R^4$, $R^5$, $R^6$, and $R^7$ are each methyl; one of one of $R^3$ and $R^8$ is hydrogen while the other is —$OR^1$, —$OC(O)R^1$, —$NHC(O)R^1$, —$N(CH_3)_3Cl$, and —$OSO_3H$.

57. The method of claim 53, wherein the catalyst is supplied to the oxidation in the form of 4-acetylamino-2,2, 6,6-tetramethylpiperidine-1-oxy or 4-acetylamino-2,2,6,6-tetramethylpiperidine-1-oxoammmonium tetrafluoroborate.

58. The method of claim 54, wherein chlorine is introduced into the oxidation in the form of gas, diluted up to about 1% by volume with an inert gas.

59. The method of claim 53, wherein the temperature of the oxidation is maintained at about 5 to about 10° C.

60. The method of claim 53, wherein the pH of the oxidation is maintained at about 11 to about 11.5.

* * * * *